(12) United States Patent
Willenberg et al.

(10) Patent No.: US 12,023,485 B2
(45) Date of Patent: Jul. 2, 2024

(54) ELECTRODE CONTACT, ELECTRODE LEAD AND ELECTRODE CONTACT SYSTEM, AND METHOD FOR CONNECTING ELECTRODE CONTACTS TO ELECTRICAL SUPPLY LEADS

(71) Applicant: BIOTRONIK SE & Co. KG, Berlin (DE)

(72) Inventors: Patrick Willenberg, Berlin (DE); Dajana Kaiser, Berlin (DE); Kerstin Taeubert, Berlin (DE); Tobias Mueller, Berlin (DE); Thomas Schaarschmidt, Schulzendorf (DE); Roland Eichberg, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 17/082,468

(22) Filed: Oct. 28, 2020

(65) Prior Publication Data

US 2021/0138237 A1 May 13, 2021

(30) Foreign Application Priority Data

Nov. 13, 2019 (EP) ..................................... 19208876

(51) Int. Cl.
*A61N 1/05* (2006.01)
(52) U.S. Cl.
CPC .................................. *A61N 1/0553* (2013.01)

(58) Field of Classification Search
CPC .. A61N 1/0553; A61N 1/37229; A61N 1/048; A61N 1/3605; A61N 1/0558; A61B 5/274
See application file for complete search history.

(56) References Cited

U.S. PATENT DOCUMENTS

| | | | | |
|---|---|---|---|---|
| 3,654,933 | A * | 4/1972 | Hagfors | A61N 1/0553 607/116 |
| 7,364,479 | B1 | 4/2008 | Deily | |
| 7,736,191 | B1 * | 6/2010 | Sochor | H01R 24/58 607/116 |
| 7,742,824 | B2 * | 6/2010 | Skubitz | A61N 1/0553 607/116 |
| 7,967,649 | B2 * | 6/2011 | Richter | H01R 13/113 439/877 |
| 8,126,529 | B2 * | 2/2012 | Johnson | A61N 1/048 600/372 |
| 10,596,368 | B2 * | 3/2020 | Renaux | A61N 1/0558 |
| 2003/0204228 | A1 * | 10/2003 | Cross, Jr. | A61N 1/0553 607/116 |

(Continued)

*Primary Examiner* — Gary Jackson
*Assistant Examiner* — Alexander M Eisenberg
(74) *Attorney, Agent, or Firm* — Buchanan Ingersoll & Rooney PC (57) ABSTRACT

An electrode contact for an electrode lead for neurostimulation comprises a contact body including a contact surface for contacting human or animal neural tissue. The electrode contact furthermore comprises an arm section for contacting at least one electrical supply lead, wherein the arm section, originating from the contact body, extends laterally in a first spatial direction which runs parallel to a main extension plane of the contact surface. The arm section includes at least one cut-out for guiding through the at least one electrical supply lead.

14 Claims, 11 Drawing Sheets

(56) References Cited

U.S. PATENT DOCUMENTS

| | | | |
|---|---|---|---|
| 2005/0090885 A1* | 4/2005 | Harris | A61N 1/0553 607/116 |
| 2006/0217777 A1* | 9/2006 | Strom | A61N 1/37512 607/36 |
| 2008/0103407 A1* | 5/2008 | Bolea | A61N 1/3606 607/42 |
| 2010/0179627 A1 | 7/2010 | Floyd et al. | |
| 2010/0198326 A1 | 8/2010 | Li | |
| 2011/0277324 A1 | 11/2011 | Conger | |
| 2016/0067477 A1* | 3/2016 | Dubuclet | A61N 1/0553 607/117 |
| 2017/0086937 A1* | 3/2017 | Tellio | A61B 90/11 |
| 2020/0316371 A1* | 10/2020 | Antonini | A61N 1/3605 |

\* cited by examiner

ELECTRODE CONTACT, ELECTRODE LEAD AND ELECTRODE CONTACT SYSTEM, AND METHOD FOR CONNECTING ELECTRODE CONTACTS TO ELECTRICAL SUPPLY LEADS

CROSS-REFERENCE TO RELATED APPLICATIONS

This patent application claims the benefit of and priority to co-pending European Patent Application No. EP 19208876.3, filed on Nov. 13, 2019 in the European Patent Office, which is hereby incorporated by reference in its entirety.

TECHNICAL FIELD

The present invention relates to an electrode contact for an electrode lead, as well as to an electrode lead for a neurostimulation application comprising such an electrode contact. The present invention furthermore relates to methods for connecting such an electrode contact to an electrical supply lead.

BACKGROUND

It is known to use implantable electrode leads for medical neurostimulation applications, such as, for example, spinal cord stimulation (SCS). Such electrode leads typically comprise one or more connectors at a proximal end for contacting an implantable pulse generator. One or more electrode contacts for contacting neural tissue are provided at a distal end of such an electrode lead. The electrode contacts, which are also referred to as electrode poles, are connected to the connectors at the distal end via electrical supply leads, for example, in the form of rope supply leads, and are thus able to transmit electrical pulses from the pulse generator to the neural tissue. For example, several such electrical supply leads can run inside an electrode lead body, which extends between the connectors and the electrode contacts from proximal to distal.

It is furthermore known that the electrode contacts of such an electrode lead can be arranged at a so-called paddle of the electrode lead. This case is also referred to as a paddle electrode lead. The paddle comprises a (for example approximately "paddle-shaped") electrically insulating paddle body extending in a flat manner, which can be made of a plastic material such as PU and/or silicone, for example.

The electrode contacts are arranged at the paddle body in such a way that in each case only one side of the electrode contact pointing toward the nerve during the application is exposed with a contact surface. The other side, together with the connected electrical supply leads, is embedded in the insulation material of the paddle body. For example, each electrode contact can be mechanically and electrically connected to a rope supply lead, wherein the rope supply leads are brought in from the respective proximal connector in one or more (for example two) electrode lead bodies.

In general, an electrode lead of the described kind requires a sufficiently secure electrical and mechanical connection of the electrical supply leads, both in the connector region and, in particular, in the region of the electrode contacts (that is, in the paddle region in the case of a paddle electrode lead).

One known solution provides that an electrical supply lead is welded onto a rear side of an electrode contact, that is, on a side of the electrode contact located opposite the contact surface, for contacting an electrode contact.

The disadvantage of this solution is that the supply lead and the retention of the electrical supply lead of each electrode contact has to take place directly before the welding process. This requires extensive manual effort or an additional automatic device. In addition, the electrical supply leads have to be cut to size in advance. This makes additional room necessary for oversized lengths of the electrical supply leads that must be allowed for, since otherwise the system could be subject to mechanical stress.

The present invention is directed toward overcoming one or more of the above-mentioned problems, though not necessarily limited to embodiments that do.

SUMMARY

It is an object of the present invention to provide an improved electrode contact for an electrode lead, which allows a secure electrical and mechanical connection of an electrical supply lead, and moreover facilitates the mounting of the electrode lead. Furthermore, an electrode lead comprising such an electrode contact, and a method for connecting such an electrode contact to an electrical supply lead are to be provided.

Proceeding from this, the subject matter of the independent claims is provided. Features of several exemplary embodiments are described in the dependent claims. The features of the dependent claims can be combined with one another to form further embodiments, unless expressly indicated otherwise.

According to a first aspect, at least the object is achieved by an electrode contact for an electrode lead. The electrode contact comprises a contact body including a contact surface for contacting human or animal neural tissue. The electrode contact furthermore comprises an arm section for contacting at least one electrical supply lead, the arm section, originating from the contact body, extending laterally in a first spatial direction that runs parallel to a main extension plane of the contact surface, and the arm section including at least one cut-out for guiding through the at least one electrical supply lead.

It is thus proposed to provide a lateral arm section on a contact body of an electrode contact. This enables a secure mechanical and electrical attachment or contacting of an electrical supply lead to or at the electrode contact.

The arm section is a "lateral" arm section in the sense that it extends, in any case also (that is, at least partially/at least with one directional component), in the first spatial direction which runs parallel to the main extension plane of the contact surface. In a top view along a second spatial direction that runs perpendicular to the main extension plane, the arm section accordingly protrudes laterally beyond the contact body.

While the contact surface is characterized by having a main extension plane, it may, apart from that, essentially take on a variety of shapes (for example, in a top view along the second spatial direction) and sizes.

When the electrode contact is arranged in a paddle of a paddle electrode lead, the main extension plane of the contact surface may, for example, coincide with a paddle plane, that is, with a main extension plane of the paddle, or run parallel thereto. The contact surface may be exposed in the process, so as to be able to make contact with nerve tissue in the surrounding area of the paddle. The remaining sections of the electrode contact, including the lateral arm, may, in contrast, be embedded into the insulation material of the paddle.

The lateral arm section provides an additional undercut, which can cause better (more secure) embedding of the electrode contact in the insulation material of the paddle.

The lateral extension of the arm section also has the advantage that the electrode contact can thus overall have a very flat design. This is in particular favorable for a use of the electrode contact in the case of a paddle electrode lead, since paddles that are customarily used are, in general, no thicker than 2 mm.

According to one embodiment, a maximum height of the contact body in the third spatial direction perpendicular to the main extension plane is smaller than a largest width of the contact body in the first spatial direction and/or than a largest width of the contact body in a second spatial direction parallel to the main extension plane. A ratio of the largest width in the third spatial direction to the largest width in the first spatial direction and/or a ratio of the largest width in the third spatial direction to the largest width in the second spatial direction, for example, can be smaller than 0.30 or 0.15, in particular smaller than 0.25 or 0.10, and preferably smaller than 0.20 or 0.08.

According to one variant, the above proportions can also apply to the electrode contact as a whole, that is, in particular including the arm section. In the event that the largest width in the third spatial direction is smaller than the largest width in the first spatial direction, and that the largest width in the second spatial direction, the electrode contact consequently has a flat basic shape. This is advantageous, for example, for an arrangement on a flat paddle of a paddle electrode lead, as described above.

As a result of the lateral arm section having a cut-out for guiding through an electrical supply lead, a mechanical fixation of the supply lead, which may be temporary if necessary, at the electrode contact is made possible. This, for example, enables a sub-assembly with a mechanical retention device for a downstream welding process, in which the supply lead is integrally and electrically conductively connected to the electrode contact. In this way, exact positioning in a relaxed position of the supply lead is made possible prior to welding, without the supply lead already having to be cut to a precise length in advance. So as to compensate for assembly tolerances, it is helpful when the length of the supply lead can be adapted, during assembly, to the actual electrode lead length. In other words, a supply lead can, for example, be mechanically retained in the correct position and in a relaxed position on an electrode contact according to the invention of a paddle electrode lead, so that the welding process and the cutting-to-size can be carried out at a later point in time.

Another advantage of the electrode contact according to the present invention, in connection with the assembly of an electrode lead, is that feeding of the electrical supply lead to the electrode contact does not have to take place directly before the welding process, but can already take place prior to that, for example, in another manufacturing location. In addition, the supply lead does not have to be held manually, or by way of a separate device, during the welding process. In this way, an easily reproducible process with reduced employee influence is possible.

The lateral arm section makes it possible, for example, during a resistance welding process, to bring the welding electrodes, on both sides, to the respective weld surface without impairment, by exposing the prefabricated paddle. In the case of a paddle comprising, usually, multiple electrode contacts (for example, 16 pieces), all connections can thus be initially mechanically retained, and thereafter they can directly be consecutively electrically contacted.

In a preferred embodiment, the arm section is designed to fix the at least one electrical supply lead in a force-fit manner when it is guided through the at least one cut-out. For example, the supply lead can be clamped in the cut-out by the tension thereof and/or under the active action of the (for example elastically deformable) arm section.

It is furthermore within the scope of the present invention that the arm section can include at least one attachment surface on which a section of the at least one electrical supply lead ends up when the supply lead is guided through the at least one cut-out. In particular, it may be provided that the at least one attachment surface is suitable for integrally attaching the section of the at least one electrical supply lead, in particular by way of welding. In other words, this is preferably a weldable attachment surface, which can also be referred to as a weld region.

In one embodiment, the arm section includes multiple, such as at least two, such cut-outs.

For example, according to one variant, the at least one cut-out can be slot-shaped. A section of the arm section can be divided by the slot-shaped cut-out(s) into multiple webs. An attachment surface of the electrode contact at the paddle which is segmented by one or more slot-shaped cut-outs can receive the supply lead(s) feed from one or more electrode lead bodies. In the process, for example, a supply lead is alternately (top/bottom) introduced through lateral slots in the arm section, which form the cut-outs. By accordingly adapting the width of the slot or slots, the supply lead is clamped and/or held in position by the generated internal stress. Thereafter, electrical contacting can be carried out by a welding process.

In another variant, the at least one cut-out is hole-shaped. For example, the at least one cut-out can be provided in the form of one or more boreholes and/or one or more passages.

In the two aforementioned variants, the slot widths or hole diameters can be deliberately selected in such a way, with respect to a diameter of the electrical supply lead that is used, that favorable mechanical retention is achieved.

In a further variant embodiment, the arm section includes one or more depressions or protuberances, which prevent the electrical supply lead from sliding away laterally.

It may furthermore be provided that the at least one cut-out is slot-shaped and divides a region of the arm section into multiple webs, wherein at least one web is obliquely positioned (for example, by an angle in the range of 10° to 30°) with respect to at least one other web.

According to a second aspect, an electrode lead for a neurostimulation application is provided. The electrode lead comprises a flat paddle, including a number of electrode contacts, for contacting human or animal neural tissue. The number of electrode contacts encompasses at least one electrode contact according to the first aspect of the present invention.

In one embodiment, the electrode lead comprises at least one electrical supply lead, which is attached to the arm section of the at least one electrode contact. For example, the at least one electrical supply lead can be integrally attached to the arm section of the at least one electrode contact, in particular byway of welding.

According to one embodiment, the electrode lead comprises at least one electrical supply lead which electrically contacts the arm section of the at least one electrode contact.

A third aspect relates to a method for connecting at least one electrode contact to at least one electrical supply lead. The electrode contact can, in particular, be an electrode contact of an electrode lead for a neurostimulation application. The method comprises providing at least one electrode contact according to the first aspect of the present invention, and attaching the at least one electrical supply lead to the arm section of the at least one electrode contact in such a way that the electrical supply lead extends through the at least one cut-out.

According to one embodiment, the at least one electrical supply lead can be integrally attached to the arm section, in particular by way of welding.

According to one embodiment, for example, the at least one cut-out can be slot-shaped and thereby divided a region of the arm section into multiple webs. Within the scope of the method according to the present invention, a section of the electrical supply lead can be placed into the at least one slot-shaped cut-out. This section can then be clamped in place by deforming at least one of the webs. In other words, at least one web can be bent so as to clamp the electrical supply lead in place on the arm section. In the process, the at least one web can, for example, be plastically deformed.

In one variant of the embodiment, a downstream welding process can be entirely dispensed with as a result of sufficient mechanical and electrical contacting of the supply lead as a consequence of the deformation of one or more webs.

In a further variant of the method according to the present invention, multiple electrode contacts according to the first aspect of the present invention are connected to one or more electrical supply leads. The electrical supply lead is, or the electrical supply leads are, initially temporarily attached to the respective arm sections of the electrode contacts so as to extend through the cut-outs in the arm sections. Optionally, a positioning of one or more of the electrical supply leads relative to the arm sections can then be adapted. Thereafter, the electrical supply lead is, or the electrical supply leads are, attached to the arm sections in the respective final position, in particular by way of welding.

According to a refinement of this variant, a further method step follows, in which the electrical supply lead is, or the electrical supply leads are, cut to size.

Additional features, aspects, objects, advantages, and possible applications of the present invention will become apparent from a study of the exemplary embodiments and examples described below, in combination with the Figures and the appended claims.

BRIEF DESCRIPTION OF THE DRAWINGS

Further advantages and embodiments of the present invention shall be described hereafter with reference to the figures. In the drawings.

DETAILED DESCRIPTION

Figure 1:
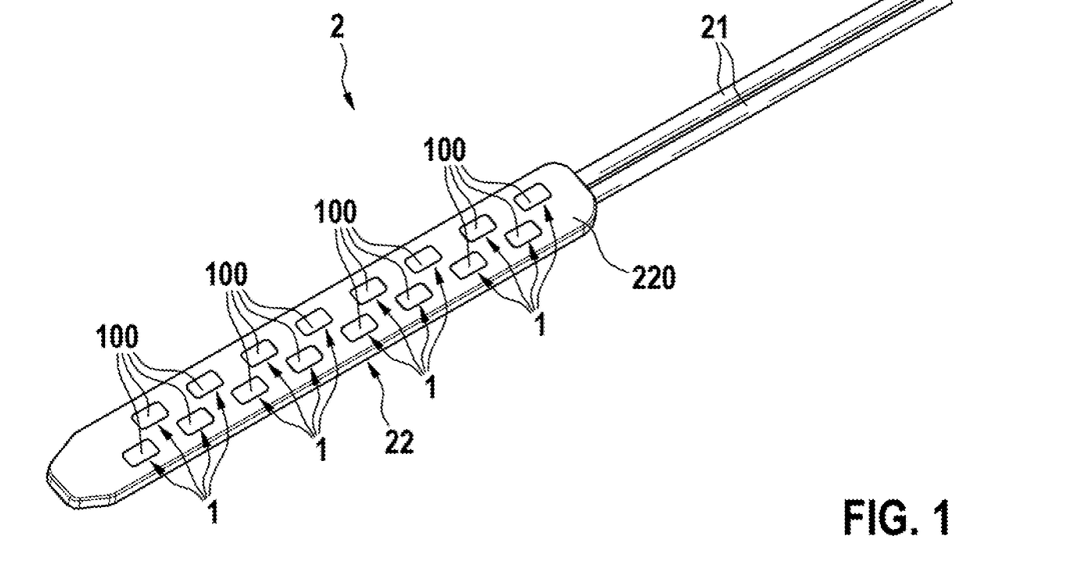
FIG. 1 schematically and by way of example shows a distal end section of an electrode lead for a neurostimulation application according to one or more embodiments.

FIG. 1 schematically and by way of example shows a distal end section of an electrode lead 2 for a neurostimulation application according to one or more embodiments.

The electrode lead 2 comprises a flat paddle 22 including multiple electrode contacts 1, which are used to electrically contact human or animal neural tissue.

The electrode contacts 1 are contacted by one or more electrical supply leads 210 (not shown individually in FIG. 1), for example in the form of rope supply leads, which are brought to the paddle 22 from proximal to distal in two electrode lead bodies 21.

The paddle 22 comprises an electrically insulating paddle body 220 extending in a flat manner, which can be made of a plastic material such as PU and/or silicone, for example. The paddle preferably has a thickness of no more than 2 mm.

The electrode contacts 1 are arranged on the paddle body 220 in such a way that in each case only one side of the electrode contact 1 pointing toward the nerve during the application is exposed with a contact surface 100. In the shown exemplary embodiment, the contact surfaces are substantially rectangular and planar, wherein the dimensions can be 3.5 mm×2.0 mm, for example. The other side of the particular electrode contact 1 is embedded, together with the connected electrical supply leads 210, into the insulation material of the paddle body 220 and accordingly not visible in FIG. 1.

Figure 2:
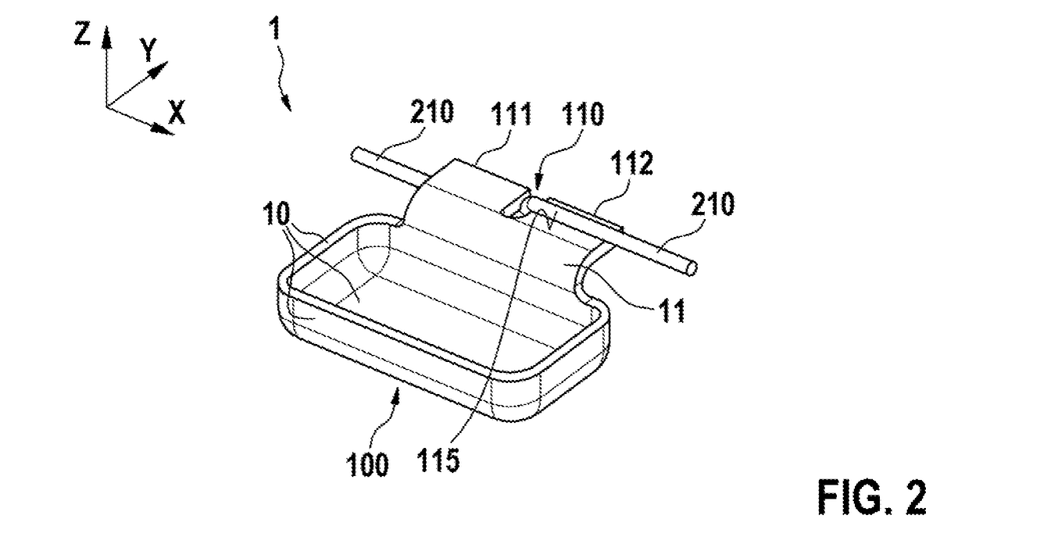
FIG. 2 schematically and by way of example shows an electrode contact according one or more embodiments.

FIG. 2 schematically and by way of example shows such an electrode contact 1 according to one or more embodiments. The perspective illustration according to FIG. 2 shows in particular the rear side of the electrode contact 1, which is not visible in the illustration in FIG. 1 since it is embedded into the paddle body 220 there. In the illustration according to FIG. 2, the contact surface 100 shown in FIG. 1 points downwardly and is not visible there per se.

The coordinate system plotted in FIG. 2 illustrates that the contact surface 100 essentially extends along a main extension plane XY. In the process, the contact surface 100 is formed by the planar bottom side of a pan-shaped contact body 10.

The electrode contact 1 comprises a lateral arm section 11, which, originating from the contact body 10, extends laterally in a first spatial direction Y, for contacting an electrical supply lead 210. The first spatial direction Y runs parallel to the main extension plane XY of the contact surface 100.

The electrode contact 1, including the lateral arm section 11, overall has a comparatively flat design. In particular, the maximum height of the electrode contact 1 in a third spatial direction Z, which is perpendicular to the main extension plane XY, is considerably smaller than a respective maximum width of the electrode contact 1 in the first spatial direction Y, and in a second spatial direction X parallel to the main extension plane XY.

The electrode contact can consist of a platinum-iridium alloy (Pt/Ir), for example, or comprise such a material.

The electrical supply lead 210 can be an insulated rope supply lead, for example, such as a DFT wire (MP35N/Ag). An outside diameter of the rope supply lead 210 can be 0.14 mm, for example.

So as to attach the electrical supply lead 210, which in the present exemplary embodiment is an insulated rope supply lead, the arm section 11 has a slot-shaped cut-out 110 on the side. The slot 110 thus formed can have a width of approximately 0.3 mm to 0.5 mm, for example.

The slot-shaped cut-out 110 divides a lateral region of the arm section 11 into a first web 111 and a second web 112. The electrical supply lead 210 is guided across the second web 112, through the slot 110, downwardly, and runs beneath the first web 111. The supply lead 210 is braced in the slot 110 and thus retained. It may additionally be welded onto a weldable attachment surface 115, which is formed by an upper side of the second web 112 and which, if necessary, can subsequently be cut to size behind the first web 111. In this way, secure and precisely fitting mechanical connection and electrical contacting of the supply lead 210 to and at the electrode contact 1 are made possible.

Figure 3:
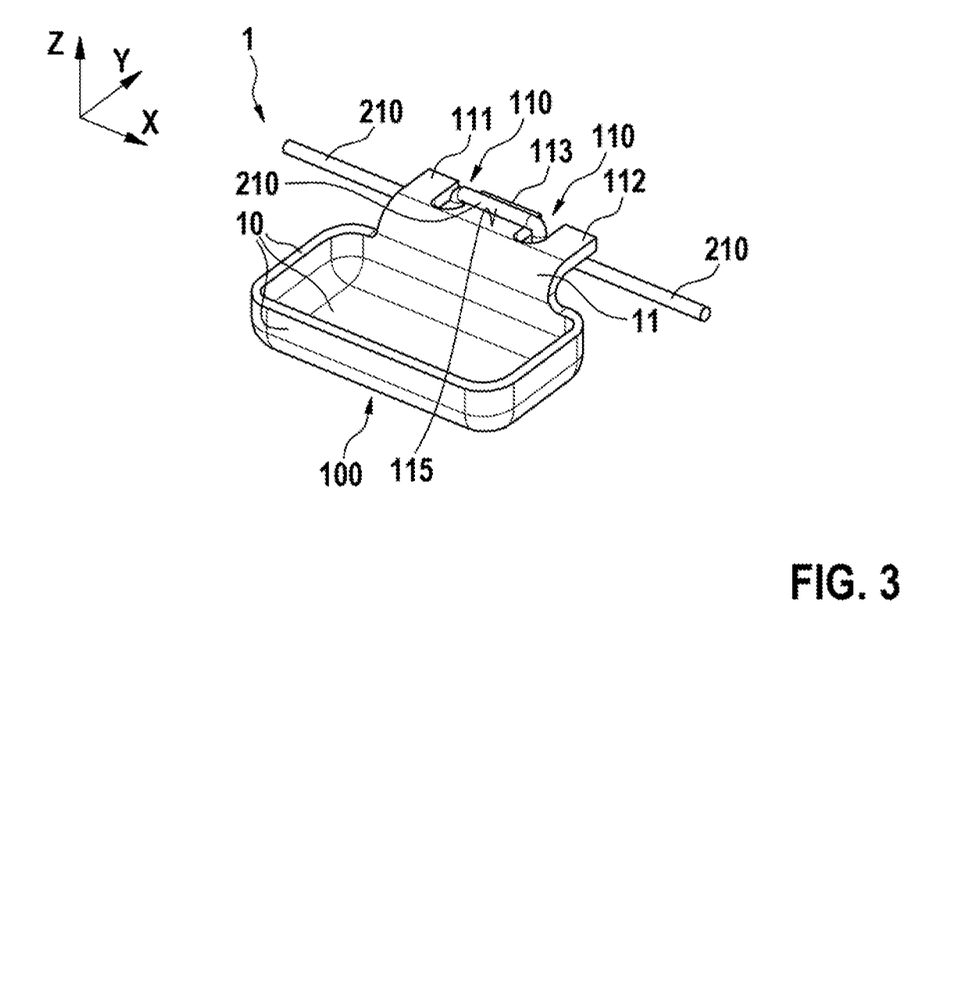
FIG. 3 schematically and by way of example shows an electrode contact according to one or more embodiments.

FIG. 3 shows a variant embodiment in which two such slots 110 are formed in the arm section 11, so that the lateral region of the arm section 11 is divided into a first web 111, a second web 112, and a (central) third web 113. In the process, the supply lead 210 is guided from beneath through one of the slots 110 upwardly, across the third web 113, and back down through the other slot 110. The supply lead 210 is braced in this alternating arrangement and thus retained. Later, it can be welded onto the attachment surface 115 formed by the top side of the third web 113 and, optionally, can be cut to length behind the first web 111.

Figure 4A:
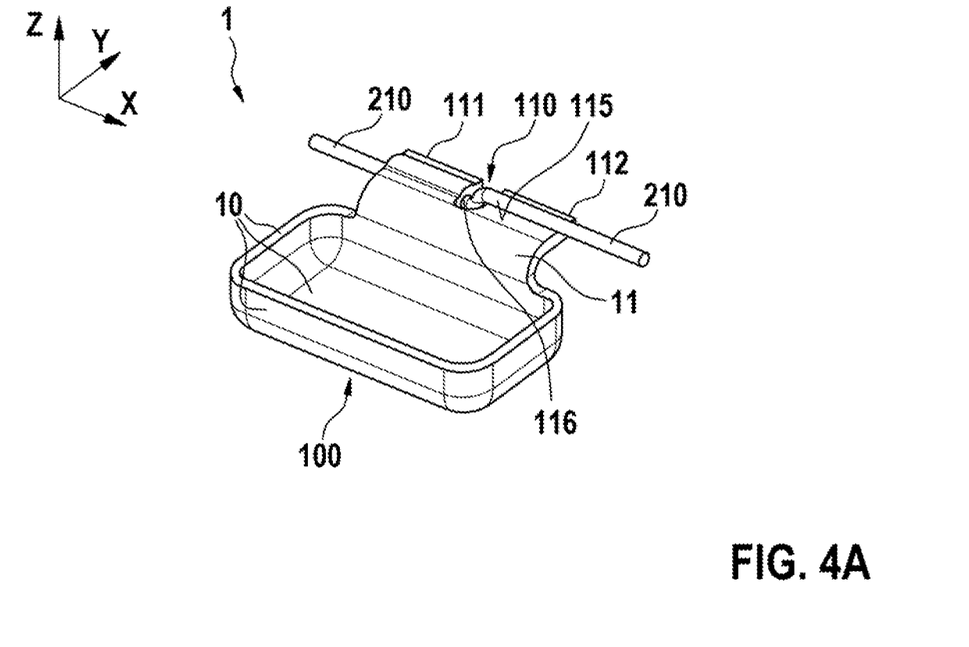
FIGS. 4A-B schematically and by way of example each show an electrode contact according to one or more embodiments.
Figure 4B:
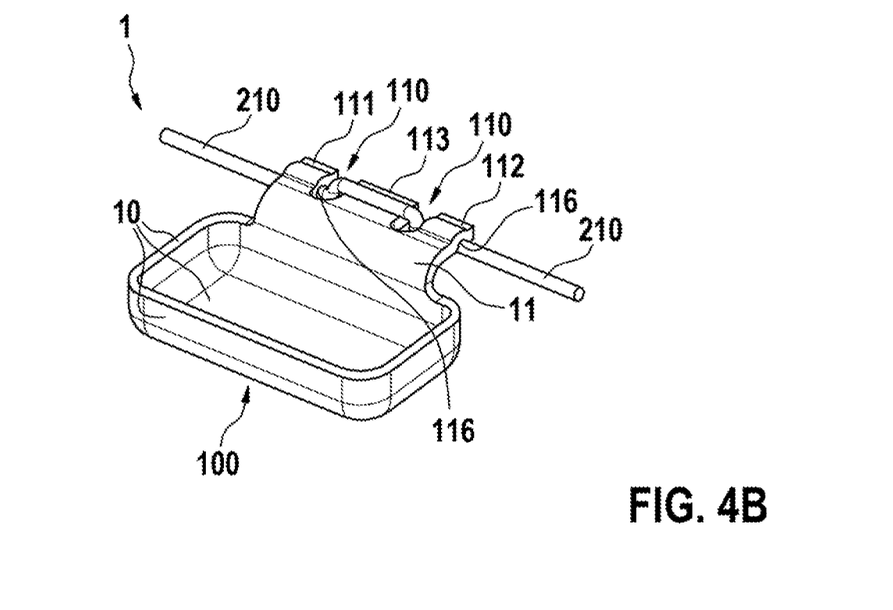

The electrode contacts 1 shown in FIGS. 4A and 4B largely correspond to the exemplary embodiments according to FIG. 2 or FIG. 3, wherein, however, depressions 116 or protuberances are additionally formed in each case in the webs 111, 112, 113 arising as a result of the slots 110, which prevent the electrical supply lead 210 from sliding away laterally.

Figure 5A:
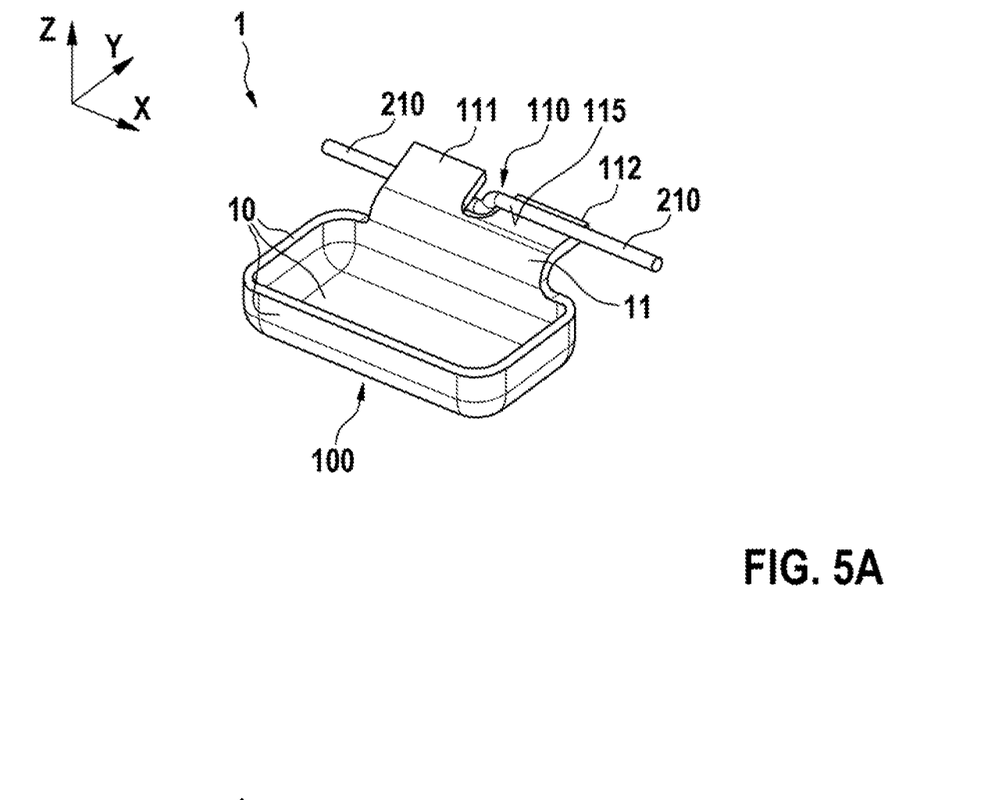
FIGS. 5A-B schematically and by way of example each show an electrode contact according to one or more embodiments.
Figure 5B:
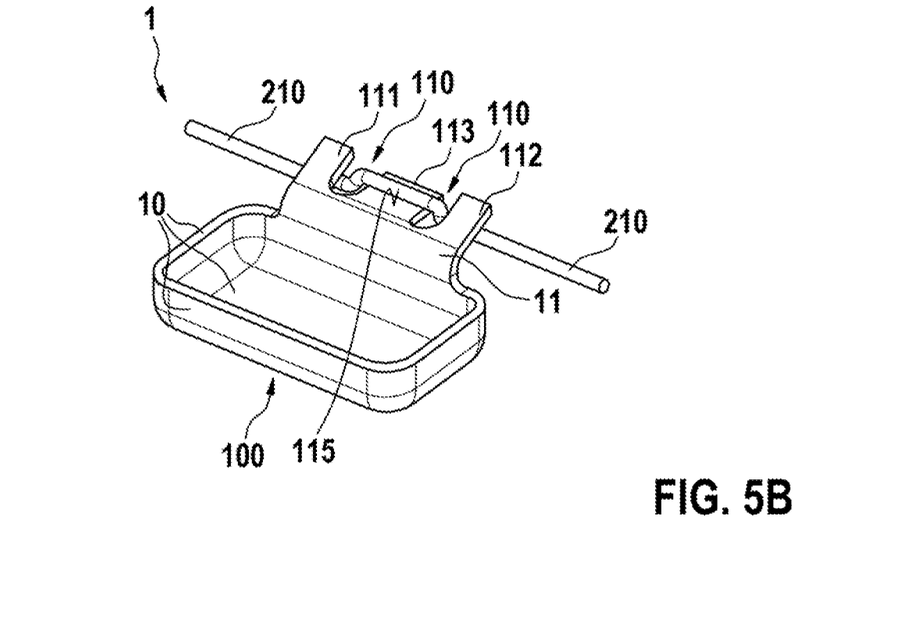

The electrode contacts 1 shown in FIGS. 5A and 5B also largely correspond to the exemplary embodiments according to FIG. 2 or FIG. 3, with the difference that the first web 111 is obliquely positioned (for example by an angle in the range of 10° to 30°) with respect to the second web 112 (in FIG. 5A), and the first web 111 and the second web 112 are obliquely positioned with respect to the third web 113 (in FIG. 5B), whereby it is made possible for the rope supply lead 210 to run through in a straight manner. For example, as is shown in FIGS. 5A-B, a web 112, 113 can be aligned substantially parallel to the main extension plane XY, whereas the other web 111 is, or the other webs 111, 112 are, angled with respect to the main extension plane XY, for example by 10 to 30°.

Figure 6A:
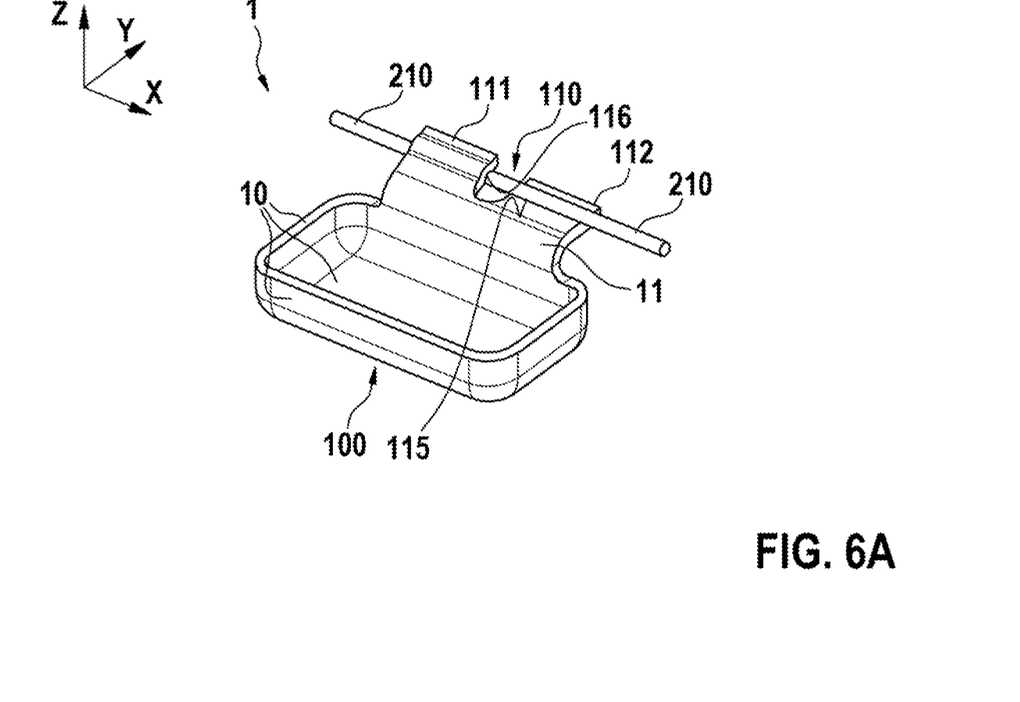
FIGS. 6A-B schematically and by way of example each show an electrode contact according to one or more embodiments.
Figure 6B:
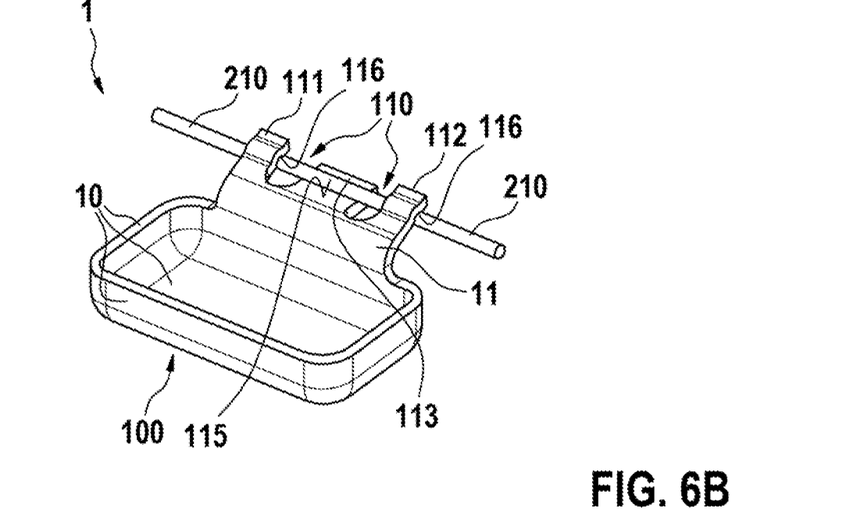
Figure 7A:
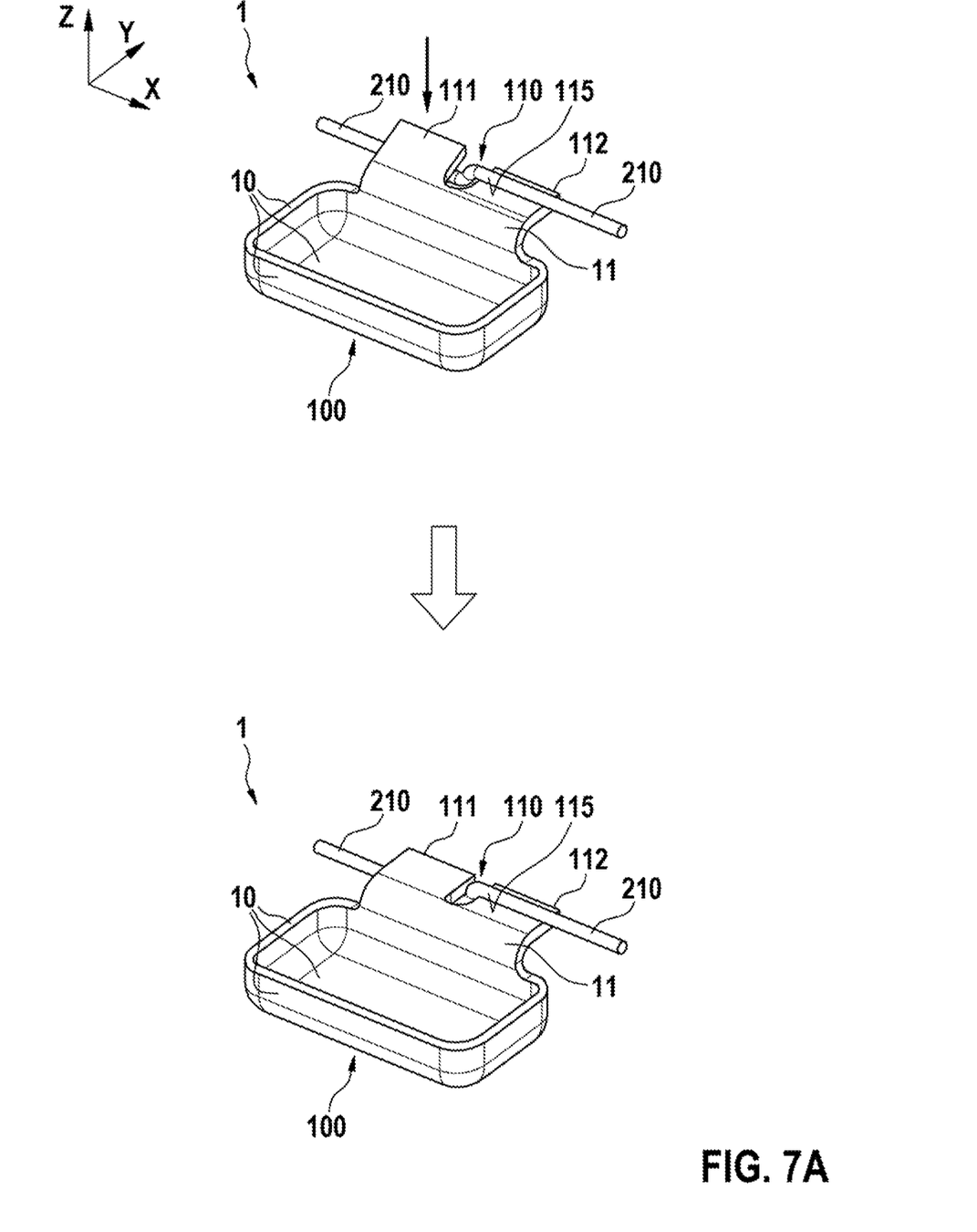
FIGS. 7A-B schematically and by way of example each show steps of a method for connecting an electrode contact to an electrical supply lead according to one or more embodiments.
Figure 7B:
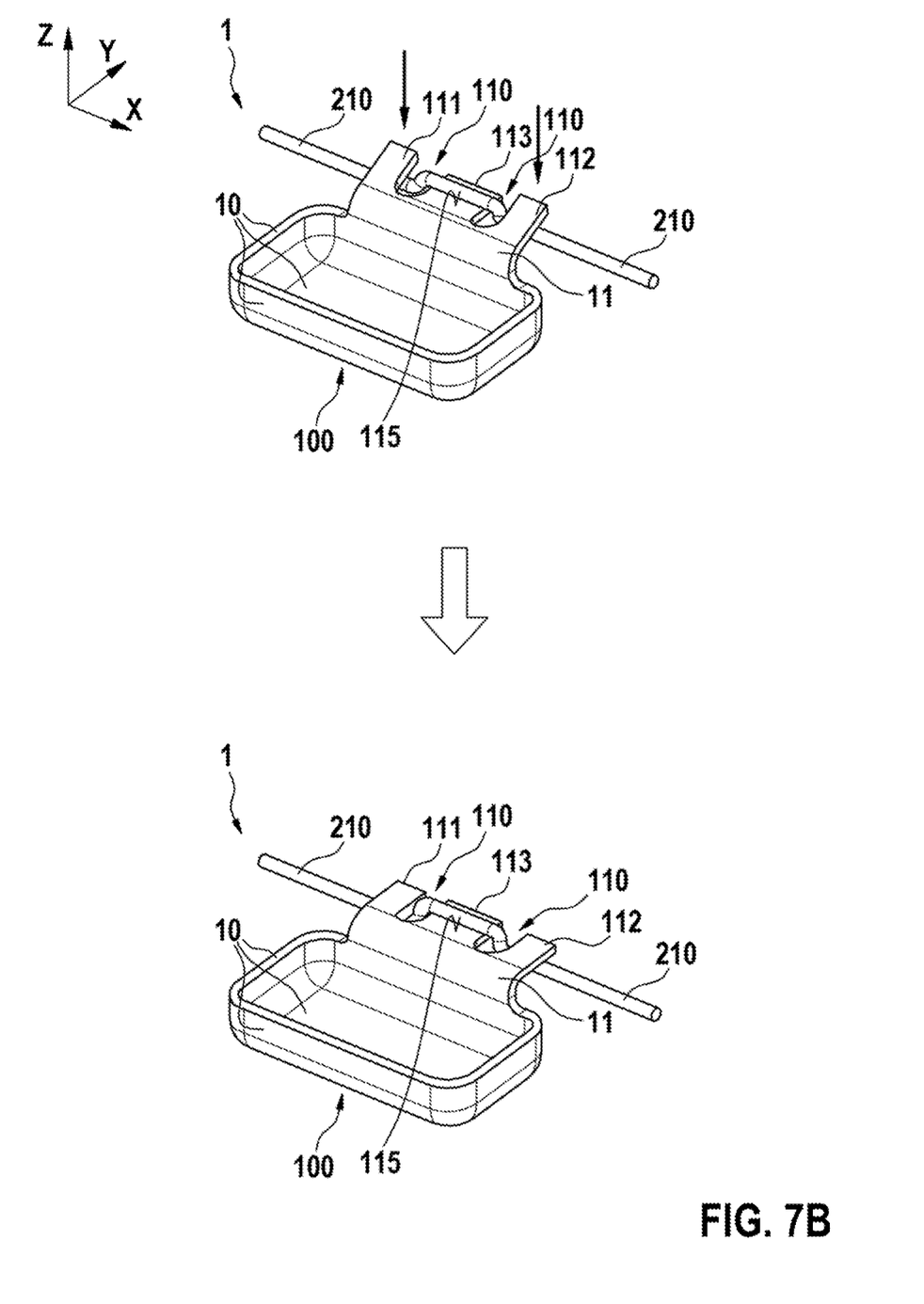
Figure 8A:
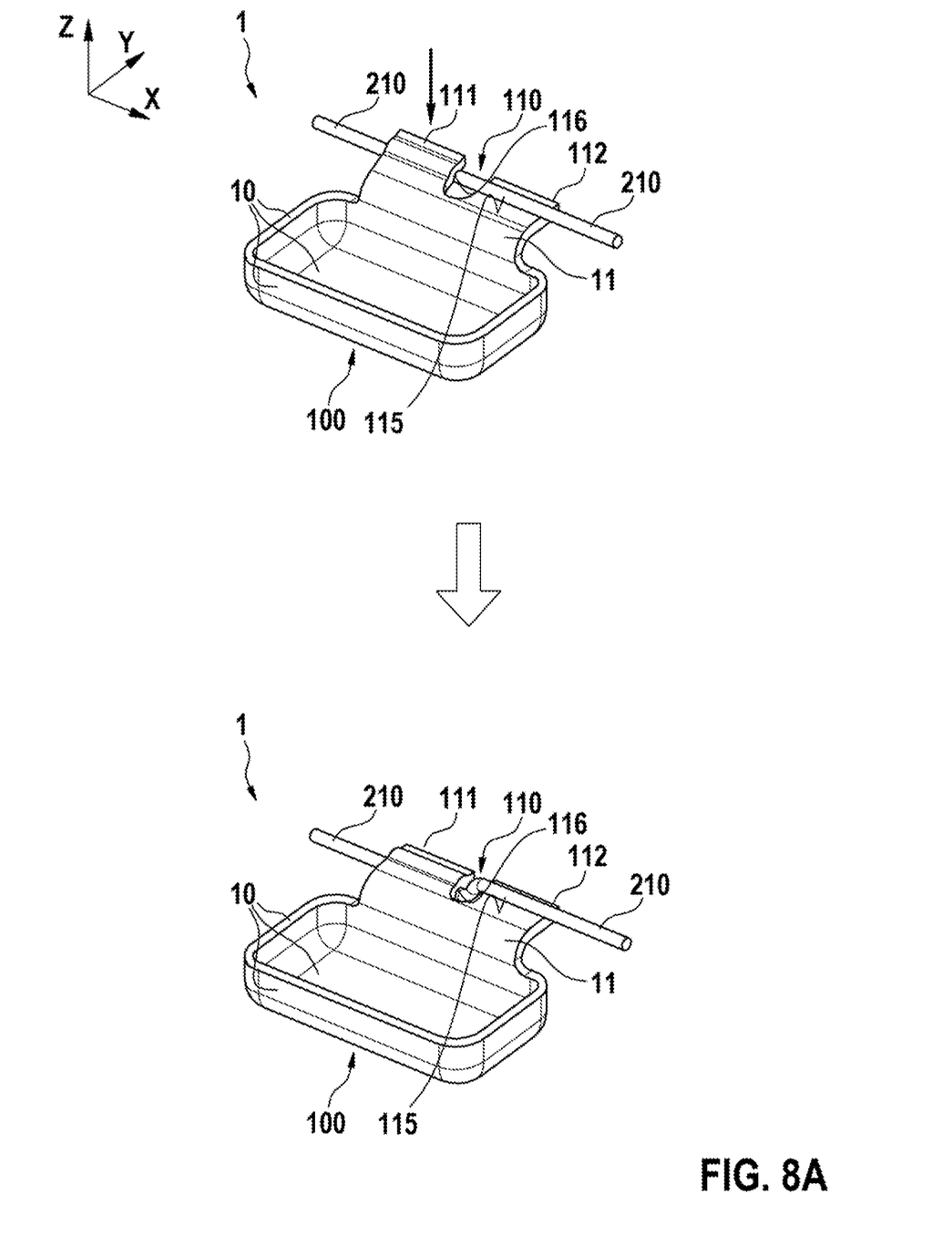
FIGS. 8A-B schematically and by way of example each show steps of a method for connecting an electrode contact to an electrical supply lead according to one or more embodiments.
Figure 8B:
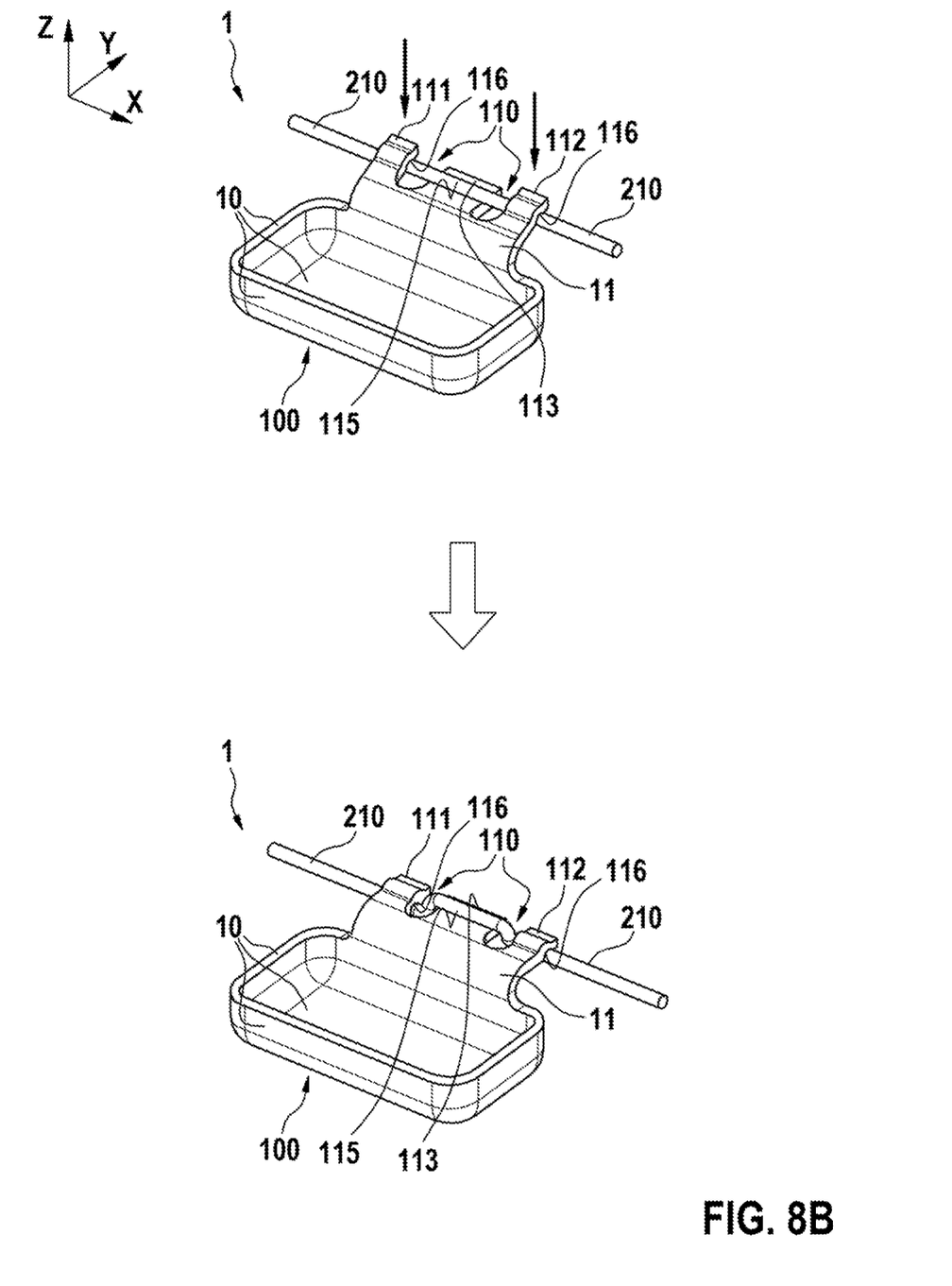

The electrode contacts 1 according to FIGS. 6A and 6B can be derived from a combination of the variant embodiments according to FIG. 4A and FIG. 5B, or according to FIG. 4B and FIG. 5B. This shall be understood to mean that a depression 116 or protuberance of the arm section 11 according to FIGS. 4A-B is combined with an oblique position of one or more webs 111, 112 according to FIGS. 5A-B.

FIGS. 7A-8B each illustrate a variant embodiment of the method according to the present invention for connecting an electrode contact 1 to an electrical supply lead 210. In the exemplary embodiments according to FIGS. 7A and 8A, the respective arm section 11 has a single slot-shaped cut-out 110, whereby two webs 111, 112 are defined. In contrast, the respective arm section 11 in the exemplary embodiments according to FIGS. 7B and 8B has two slot-shaped cut-outs 110, so that in each case three webs 111, 112, 113 result. Additionally, a depression 116 is provided in the case of the arm sections 11 according to FIGS. 8A-B.

In a respective top image portion of FIGS. 7A-8B, it is illustrated that initially a section of the supply lead 210 is placed into the slot-shaped cut-out(s) 110 for attaching the electrical supply lead 210. Initially, one or more of the webs 111, 112 are obliquely positioned with respect to the remaining webs 112, 113. In this way, the supply lead 210 can be easily inserted into the respective cut-out(s).

The section of the supply lead 210 is then clamped between the webs 111, 112 by deforming at least one of the webs 111, 112, 113, as is shown in a respective lower image portion of FIGS. 7A-8B. In other words, at least one web 111, 112 is bent so as to clamp the electrical supply lead 210 in place on the arm section 11. In the process, the at least one web 111, 112 can, for example, be plastically deformed.

In one variant of the embodiment, a downstream welding process can be entirely dispensed with as a result of sufficient mechanical and electrical contacting of the supply lead 210 as a consequence of the deformation of the web or webs 111, 112.

Figure 9A:
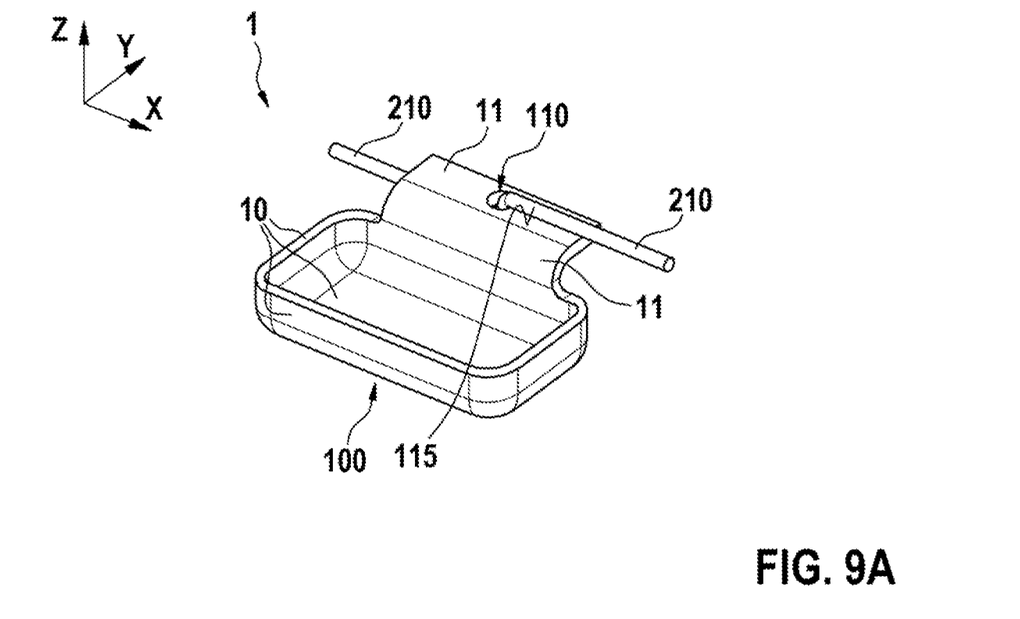
FIGS. 9A-B schematically and by way of example each show an electrode contact according to one or more embodiments.
Figure 9B:
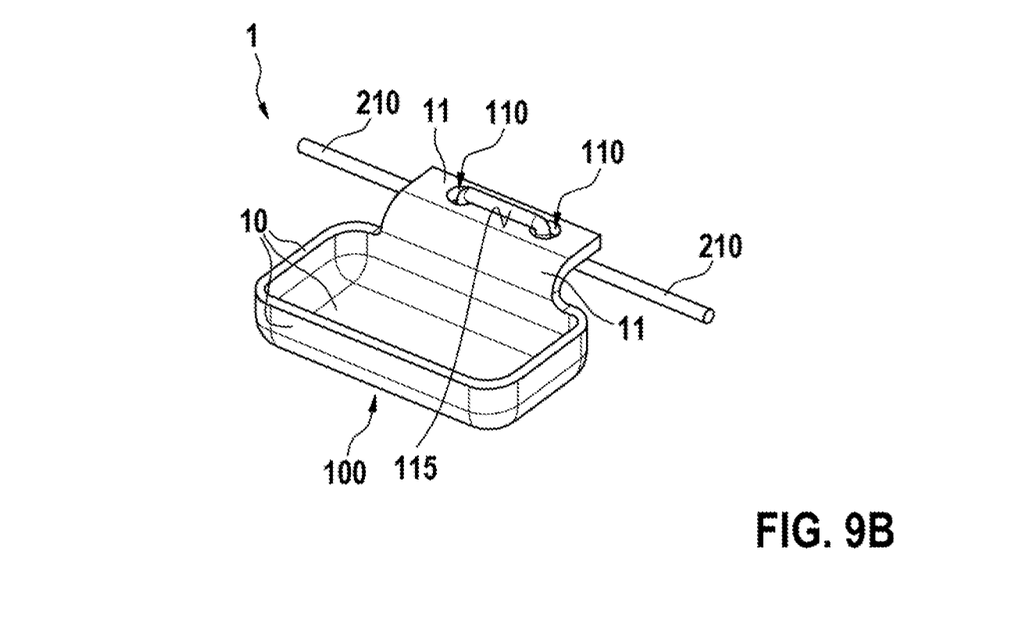

The electrode contacts 1 shown in FIGS. 9A and 9B, in principle, correspond to the exemplary embodiments according to FIG. 2 or FIG. 3 described above, with the difference that the cut-outs 110 are not slot-shaped, but hole-shaped. In other words, the slots 110 are replaced here by boreholes or passages 110. Accordingly, the electrical supply lead 210 is not inserted from the side in these embodiments, but is guided directly through the hole-shaped cut-outs 110.

Figure 10:
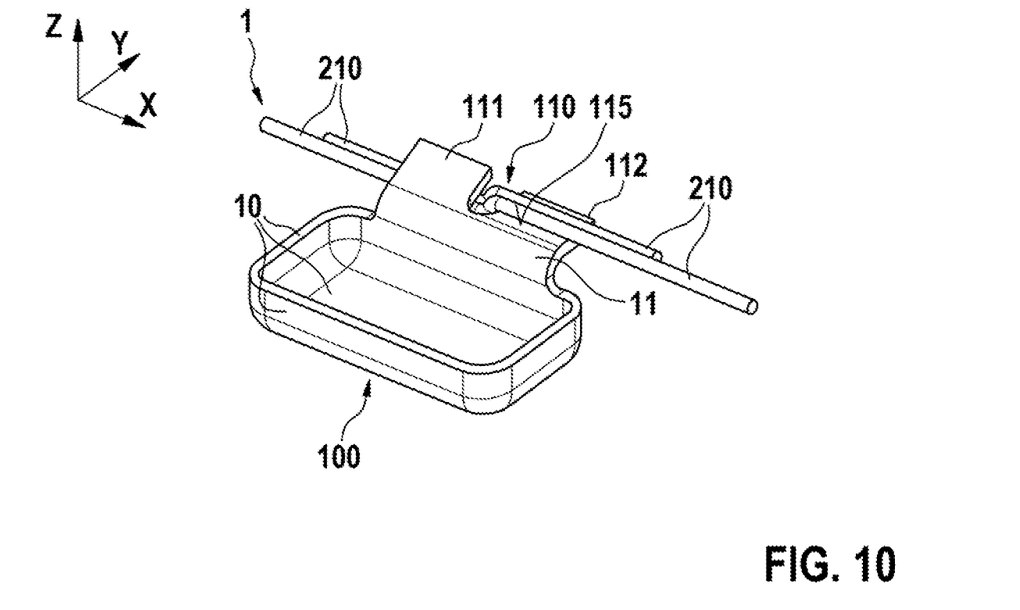
FIG. 10 schematically and by way of example shows an electrode contact according to one or more embodiments, which is connected to two electrical supply leads.

FIG. 10 illustrates an embodiment in which two parallel supply leads 210 are attached to the lateral arm section 11 of an electrode contact 1 in the manner described above. In principle, it is also possible for more than two parallel supply leads 210 to be provided, wherein the webs 111, 112 or the slot 110, through which the supply leads 210 are guided, can be extended as needed in the first spatial direction Y so as to provide sufficient room for the multiple supply leads 210.

Figure 11:
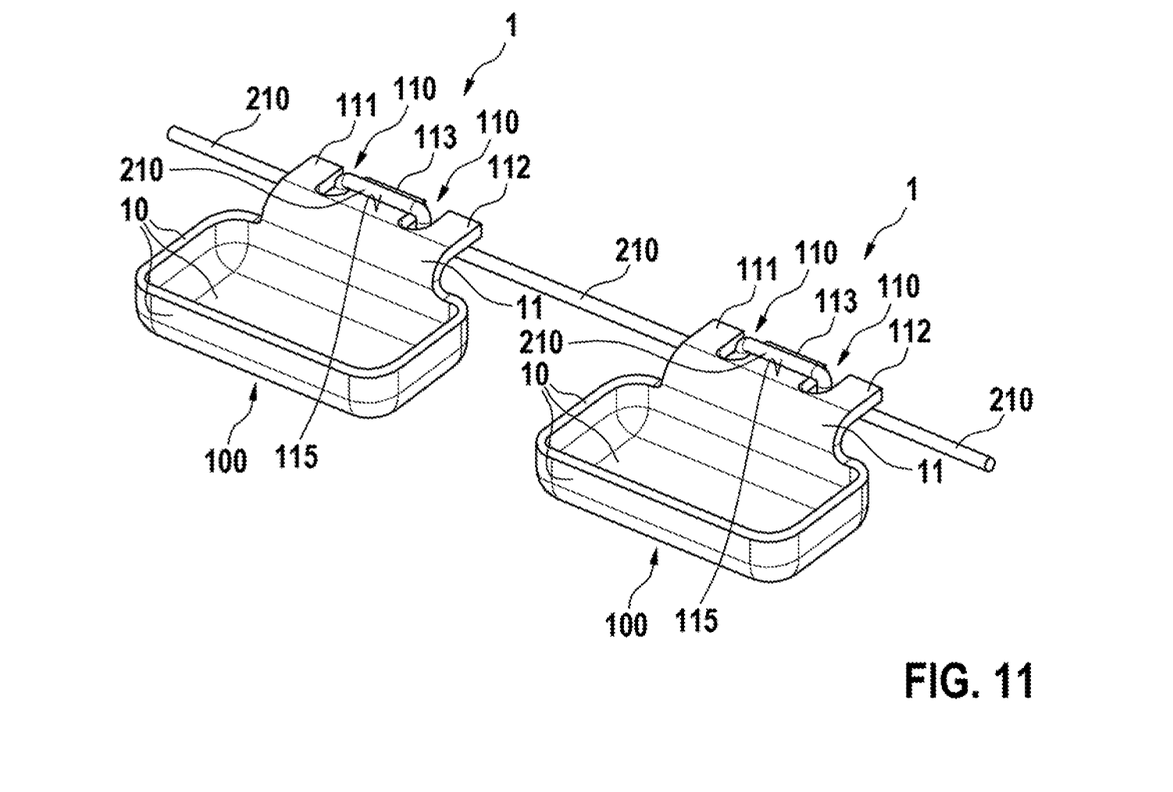
FIG. 11 schematically and by way of example shows two electrode contacts according to one or more embodiments, which are connected to a shared electrical supply lead.

The supply lead guidance can, of course, also be continued across multiple electrode contacts 1, in such a way that a supply lead 210 is sequentially connected to multiple electrode contacts 1. In FIG. 11, this is illustrated, for example, by a supply lead 210 and two electrode contacts 1 connected thereto.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this disclosure, which is to be given the full breadth thereof.

Additionally, the disclosure of a range of values is a disclosure of every numerical value within that range, including the end points.

LIST OF REFERENCE NUMERALS 1 electrode contact
10 contact body
100 contact surface
11 arm section
110 cut-out
111 first web
112 second web
113 third web
115 attachment surface
116 depression
2 electrode lead
21 electrode lead body
210 electrical supply lead
22 paddle
220 paddle body
X second spatial direction
Y first spatial direction
Z third spatial direction
XY main extension plane

What is claimed is:

1. An electrode contact for an electrode lead for neurostimulation, the electrode contact comprising:
   a contact body including a contact surface configured to contact human or animal neural tissue, and
   an arm section integrally formed with the contact body and configured to contact at least one electrical supply lead, the arm section, originating from the contact body, extending laterally in a first spatial direction that extends away from the contact body and runs parallel to a main extension plane of the contact surface, and the arm section including at least one cut-out configured to guide through the at least one electrical supply lead,
   wherein the at least one cut-out is a slot-shaped cut-out which divides the arm section into a plurality of webs having oppositely facing attachment surfaces,
   wherein the arm section is configured to guide the at least one electrical supply lead through the at least one cut-out such that the at least one electrical supply lead makes physical contact with each oppositely facing attachment surface.

2. The electrode contact according to claim 1, wherein a maximum height of the contact body in a third spatial direction perpendicular to the main extension plane is less than:
   a largest width of the contact body in the first spatial direction, and/or
   a largest length of the contact body in a second spatial direction parallel to the main extension plane.

3. The electrode contact according to claim 1, wherein the arm section is designed to fix the at least one electrical supply lead in a force-fit manner when it is guided through the at least one cut-out.

4. The electrode contact according to claim 1, wherein at least one of the plurality of webs includes an attachment surface on which a section of the at least one electrical supply lead contacts when the supply lead is guided through the at least one cut-out, wherein the attachment surface is configured to integrally attach the section of the at least one electrical supply lead by way of welding.

5. The electrode contact according to claim 1, wherein the plurality of webs include depressions formed therein, wherein the at least one electrical supply lead is received in the depressions.

6. The electrode contact according to claim 5, wherein the depressions are configured to prevent lateral movement of the at least one electrical supply lead.

7. An electrode lead for a neurostimulation application, wherein the electrode lead comprises:
   a flat paddle including a number of electrode contacts configured to contact human or animal neural tissue, wherein the number of electrode contacts encompasses at least one electrode contact according to claim 1.

8. The electrode lead according to claim 7, the electrode lead comprising at least one electrical supply lead, wherein the at least one electrical supply lead is attached to the arm section of the at least one electrode contact.

9. The electrode lead according to claim 8, wherein the at least one electrical supply lead is integrally attached to the arm section of the at least one electrode contact by way of welding.

10. The electrode lead according to claim 7, the electrode lead comprising at least one electrical supply lead, wherein the at least one electrical supply lead electrically contacts the arm section of the at least one electrode contact.

11. A method for connecting at least one electrode contact to at least one electrical supply lead, the method comprising:
    providing at least one electrode contact according to claim 1; and
    attaching the at least one electrical supply lead to the arm section of the at least one electrode contact in such a way that the electrical supply lead extends through the at least one cut-out.

12. The method according to claim 11, wherein the at least one electrical supply lead is integrally attached to the arm section by way of welding.

13. The method according to claim 11, the method further comprising:
    inserting a section of the electrical supply lead into the at least one slot-shaped cut-out; and
    clamping the section of the electrical supply lead by deforming at least one of the plurality of webs.

14. The method according to claim 11, multiple such electrode contacts being connected to one or more electrical supply leads, the method further comprising:
    initially temporarily attaching the electrical supply lead or the electrical supply leads to the respective arm sections of the electrode contacts so as to extend through the cut-outs in the arm sections;
    thereafter, optionally adapting the positioning of one or more of the electrical supply leads relative to the arm sections; and
    thereafter, attaching the electrical supply lead or the electrical supply leads to the arm sections in the respective final position by way of welding.

* * * * *